(12) United States Patent
Nissila et al.

(10) Patent No.: US 9,370,691 B2
(45) Date of Patent: Jun. 21, 2016

(54) APPARATUS FOR METABOLIC TRAINING LOAD, MECHANICAL STIMULUS, AND RECOVERY TIME CALCULATION

(75) Inventors: Juuso Samuel Nissila, Li (FI); Hannu Olavi Kinnunen, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 674 days.

(21) Appl. No.: 12/934,009

(22) PCT Filed: Mar. 27, 2009

(86) PCT No.: PCT/IB2009/005151
§ 371 (c)(1),
(2), (4) Date: Oct. 4, 2010

(87) PCT Pub. No.: WO2009/118645
PCT Pub. Date: Oct. 1, 2009

(65) Prior Publication Data
US 2011/0021319 A1 Jan. 27, 2011

Related U.S. Application Data

(60) Provisional application No. 61/040,025, filed on Mar. 27, 2008.

(51) Int. Cl.
*A63B 24/00* (2006.01)
*A61B 5/22* (2006.01)
(Continued)

(52) U.S. Cl.
CPC ............. *A63B 24/0062* (2013.01); *A61B 5/222* (2013.01); *A61B 5/4866* (2013.01);
(Continued)

(58) Field of Classification Search
CPC ........... A63B 24/0062; A63B 24/0072; A63B 2024/0065; A63B 2220/30; A63B 2230/00; A63B 2230/06; A63B 2230/50; A63B 2230/70; A63B 2230/75; A63B 5/222; A63B 5/4866; A63B 5/024
USPC ...................... 482/1, 8–9; 600/481, 483, 587; 73/379.01; 700/91; 340/573.1
See application file for complete search history.

(56) References Cited

U.S. PATENT DOCUMENTS 6,537,227 B2 * 3/2003 Kinnunen et al. ............ 600/500
6,540,686 B2 * 4/2003 Heikkila et al. .............. 600/483
(Continued)

OTHER PUBLICATIONS

McArdle, William D., Frank I. Katch, and Victor L. Katch. "Chapter 1: Carboydrates, Lipids, and Proteins." Exercise Physiology: Energy, Nutrition, and Human Performance. Philadelphia: Lippincott Williams & Wilkins, 2001. 6-43.*
(Continued)

*Primary Examiner* — Oren Ginsberg
*Assistant Examiner* — Sundhara Ganesan
(74) *Attorney, Agent, or Firm* — Hoffman & Bacon, LLP (57) ABSTRACT

A method of determining a user's training load, includes determining protein combustion information and determining the user's training load based on the protein combustion information. The protein combustion information may be determined using heart rate information, activity information, carbohydrate reserve information determined using a carbohydrate combustion model and carbohydrate reserve information representing the user's carbohydrate reserves at a beginning of at least one exercise session, fitness information, intensity information, nutritional intake information representing nutritional intake during at least one exercise session, and/or a fat combustion model. The user's training load may be determined based on a mechanical stimulus and/or a modality. Recovery time information may be determined based on the training load. A corresponding apparatus and computer-readable medium correspond to the above method.

24 Claims, 6 Drawing Sheets

(51) Int. Cl.
*A61B 5/00* (2006.01)
*A61B 5/024* (2006.01)

(52) U.S. Cl.
CPC ............ *A61B 5/024* (2013.01); *A63B 24/0075* (2013.01); *A63B 2024/0065* (2013.01); *A63B 2220/30* (2013.01); *A63B 2230/00* (2013.01); *A63B 2230/06* (2013.01); *A63B 2230/50* (2013.01); *A63B 2230/70* (2013.01); *A63B 2230/75* (2013.01)

(56) References Cited

U.S. PATENT DOCUMENTS

| | | | |
|---|---|---|---|
| 6,554,776 B1 | 4/2003 | Snow et al. | |
| 6,687,535 B2* | 2/2004 | Hautala et al. | 600/520 |
| 7,534,206 B1* | 5/2009 | Lovitt et al. | 600/300 |
| 7,641,592 B2* | 1/2010 | Roche | 482/9 |
| 8,052,580 B2* | 11/2011 | Saalasti et al. | 482/8 |
| 8,066,514 B2* | 11/2011 | Clarke | 434/247 |
| 8,348,809 B2* | 1/2013 | van der Zande et al. | 482/8 |
| 2002/0107433 A1* | 8/2002 | Mault | 600/300 |
| 2003/0013995 A1 | 1/2003 | Oshima et al. | |
| 2006/0032315 A1* | 2/2006 | Saalastic et al. | 73/808 |
| 2006/0063980 A1* | 3/2006 | Hwang et al. | 600/300 |
| 2006/0281606 A1* | 12/2006 | Radow | 482/54 |
| 2007/0026999 A1* | 2/2007 | Merolle et al. | 482/8 |
| 2007/0082789 A1* | 4/2007 | Nissila et al. | 482/8 |
| 2008/0300498 A1* | 12/2008 | Edwards | 600/520 |
| 2009/0069156 A1* | 3/2009 | Kurunmaki et al. | 482/9 |

OTHER PUBLICATIONS

Hampus Lundblad, International Search Report PCT/ISA/210 for corresponding PCT application No. PCT/IB2009/005151, pp. 1-6 (Jul. 29, 2009).

* cited by examiner

APPARATUS FOR METABOLIC TRAINING LOAD, MECHANICAL STIMULUS, AND RECOVERY TIME CALCULATION

CROSS REFERENCE TO RELATED APPLICATION

This application is a National Phase application of International Application No. PCT/IB2009/005151, filed Mar. 27, 2009, which claims the benefit of U.S. Provisional Application Ser. No. 61/040,025 entitled "Metabolic Training Load, Mechanical Training Load and Recovery Calculation", filed Mar. 27, 2008, the disclosures of which are incorporated herein by reference in their entirety.

BACKGROUND

1. Field

The present application generally relates to a method and apparatus that determine various parameters associated with a user during exercise or training sessions, and more specifically relates to a method and system that calculates training load, mechanical stimulus, and/or recovery time.

2. Brief Description of the Related Art

Conventional methods of monitoring the extent and intensity of training and exercise sessions have not adequately or accurately dealt with determinations of training load, mechanical or training stimulus, and the time necessary to adequately recover from training sessions. The conventional methods, such as EPOC (Excess Post-exercise Oxygen Consumption) are based on a lactate burning model, which is characterized by the amount of oxygen consumed during recovery in excess of that which would have ordinarily been consumed at rest following cardiovascular exercise. The drawbacks of the known methods are inaccuracy and insensitivity to exercise history. The process is further complicated when the determination is to be made with respect to multiple training sessions incorporating different exercise or training modalities, such as continuous training, intermittent training, strength training, or training through participation in various sports or activities, such as running, swimming, and cycling.

SUMMARY

The application includes three aspects, which are linked to each other. These aspects are (a) training load, (b) mechanical stimulus, and (c) recovery time.

The training load characterizes the physical load experienced by a user in response to an exercise. In an embodiment, a training load model accounts for protein consumption during the exercise. The protein consumption may be considered as a function of carbohydrate reserves at each time instant during the exercise. Thus, the protein calculation may be based on knowledge of the carbohydrate state at the beginning of exercise, the carbohydrate reload during the exercise, and carbohydrate consumption during the exercise.

The mechanical or training stimulus characterizes the mechanical stress experienced by the user.

The recovery time is the time the user needs for recovering from the exercise to a predefined level of recovery. The predefined level of recovery may be expressed in terms of energy reserves, which the person has gained during the recovery period, or a predicted muscle pain or inflammation level.

In an embodiment of the invention, the training load is expressed in terms of recovery time.

A method of determining a user's physical or training load in accordance with the present application includes determining the user's instantaneous protein expenditure during an exercise, and determining the user's physical load by using the instantaneous protein expenditure.

The method may also include any one or more of the following features: determining the user's instantaneous protein expenditure during an exercise by using the user's heart rate information or activity information, determining the user's instantaneous protein expenditure by using the user's prevailing carbohydrate reserve, determining the user's prevailing carbohydrate reserve by using a carbohydrate combustion model and carbohydrate reserve at the beginning of the exercise, determining the user's protein expenditure by using the user's fitness level, determining the user's protein expenditure by using the user's intensity data, determining the user's protein expenditure by using the user's threshold variables, determining the user's instantaneous protein expenditure by using nutritional intake information during the exercise, determining the user's instantaneous protein expenditure by using a fat combustion model during the exercise, determining the user's physical load by accounting for the mechanical stimulus of the exercise, determining the user's physical load by using a training modality of the exercise, displaying the training load on a display device, and estimating the user's exercise recovery characteristics on the basis of the training load.

The method of the present application described above may be implemented in an apparatus incorporating any or all of the above features. The apparatus may be selected from a group including a mobile phone, a sport computer, a circuit board, exercise equipment, a wrist device, a heart rate transmitter, and a base station configured to receive heart rate information from one or more users. The method of the present application described above may be implemented using a computer program including coded instructions for executing a computer process in a computing device, which computer process implements the method incorporating any or all of the above features.

A method of determining a user's mechanical stimulus from an exercise in accordance with the present application includes determining the user's mechanical stimulus by using heart rate information or activity information.

The method may also include any one or more of the following: determining the user's mechanical stimulus by using the mode (such as continuous, intermittent, strength, or a particular sport or activity) of the exercise, wherein the mode of the exercise may be characterized by a flexpoint of the exercise, determining the user's mechanical stimulus by using the user's adaptation to exercise, determining the user's instantaneous mechanical stimuli during the exercise, determining the user's mechanical stimulus by using the instantaneous mechanical stimuli, and determining the user's mechanical stimulus by using the effect of an accumulation of mechanical stimulus on the heart rate information.

The method of determining a user's mechanical stimulus from an exercise in accordance with the present application may be implemented in an apparatus incorporating any or all of the above features. The apparatus may be selected from a group including a mobile phone, a sport computer, a circuit board, exercise equipment, a wrist device, a heart rate transmitter, and a base station configured to receive heart rate information from one or more user's. The method determining a user's mechanical stimulus from an exercise may be implemented using a computer program including coded instructions for executing a computer process in a computing device, which computer process implements the method incorporating any or all of the above features.

A method of estimating a user's exercise recovery time characteristics in accordance with the present application includes estimating the user's exercise recovery time on the basis of training load of at least one exercise. The training load is characterized by at least one of the user's protein expenditure during at least one exercise, the user's carbohydrate expenditure during at least one exercise, the user's fat or lipid expenditure during at least one exercise, and the user's mechanical stimulus caused by at least one exercise.

The method may also include estimating the user's exercise recovery on the basis of at least one of the user's protein expenditure during at least one exercise during the recovery period, the user's carbohydrate expenditure during at least one exercise during the recovery period, the user's fat or lipid expenditure during at least one exercise during the recovery period, and the user's mechanical stimulus caused by at least one exercise during the recovery period. The method may also include estimating the user's exercise recovery on the basis of at least one of the user's protein expenditure during at least one exercise before the recovery period, the user's carbohydrate expenditure during at least one exercise before the recovery period, the user's fat or lipid expenditure during at least one exercise before the recovery period, and the user's mechanical stimulus caused by at least one exercise before the recovery period. The recovery characteristics may be defined by recovery time, and the recovery characteristics may be defined by the user's recovery condition at a given time instant. The method may further include estimating the user's exercise recovery on the basis of carbohydrate reserves after the exercise, estimating the user's exercise recovery on the basis of a carbohydrate reload model, and determining the user's mechanical stimulus by using the effect of an accumulation of mechanical stimulus to the heart rate information.

The method of estimating a user's exercise recovery time in accordance with the present application may be implemented in an apparatus incorporating any or all of the above features. The apparatus may be selected from a group including a mobile phone, a sport computer, a circuit board, exercise equipment, a wrist device, a heart rate transmitter, and a base station configured to receive heart rate information from one or more user's. The method of estimating a user's exercise recovery may be implemented using a computer program including coded instructions for executing a computer process in a digital processor, which computer process implements the method incorporating any or all of the above features. In accordance with the application, a method of determining a user's training load is described, which includes determining protein combustion information associated with the user in a first computer process, and determining the user's training load based on the protein combustion information in a second computer process. The protein combustion information may be determined using heart rate information and/or activity information, wherein the heart rate information and intensity information are associated with the user. The protein combustion information may be determined using carbohydrate reserve information associated with the user, which is determined using a carbohydrate combustion model and carbohydrate reserve information representing the user's carbohydrate reserves at a beginning of at least one exercise session. The protein combustion information may be determined using fitness information associated with the user, intensity information associated with the user, nutritional intake information associated with the user representing nutritional intake during at least one exercise session, and/or a fat combustion model. The user's training load may be determined based on a mechanical stimulus associated with at least one exercise session, and/or a modality associated with at least one exercise session. The training load may be displayed on a display device. Recovery time information may be determined based on the training load.

In further accordance with the application, an apparatus to determine a user's training load is provided, which includes a protein combustion determination unit to determine protein combustion information associated with the user, and a training load determination unit to determine the user's training load based on the protein combustion information. The protein combustion determination unit may determine the protein combustion information using heart rate information, activity information, and/or carbohydrate reserve information. The protein combustion determination unit may determine the carbohydrate reserve information using a carbohydrate combustion model and carbohydrate reserve information representing the user's carbohydrate reserves at a beginning of at least one exercise session.

In still further accordance with the application, a computer-readable storage medium including instructions thereon is provided that, when executed by a computing device, cause the computing device to determine protein combustion information associated with the user, and determine the user's training load based on the protein combustion information. The computer-readable storage medium may further comprise instructions that, when executed by the computing device, cause the computing device to determine the protein combustion information using at least one of heart rate information and activity information, and/or carbohydrate reserve information associated with the user. The computer-readable storage medium may further comprise instructions that, when executed by the computing device, cause the computing device to determine the carbohydrate reserve information using a carbohydrate combustion model and carbohydrate reserve information, the carbohydrate reserve information representing the user's carbohydrate reserve at a beginning of at least one exercise session.

Other objects and features of the present application will become apparent from the following detailed description considered in conjunction with the accompanying drawings. It is to be understood, however, that the drawings are designed as an illustration only and not as a definition of the limits of the application.

DETAILED DESCRIPTION

Figure 1:
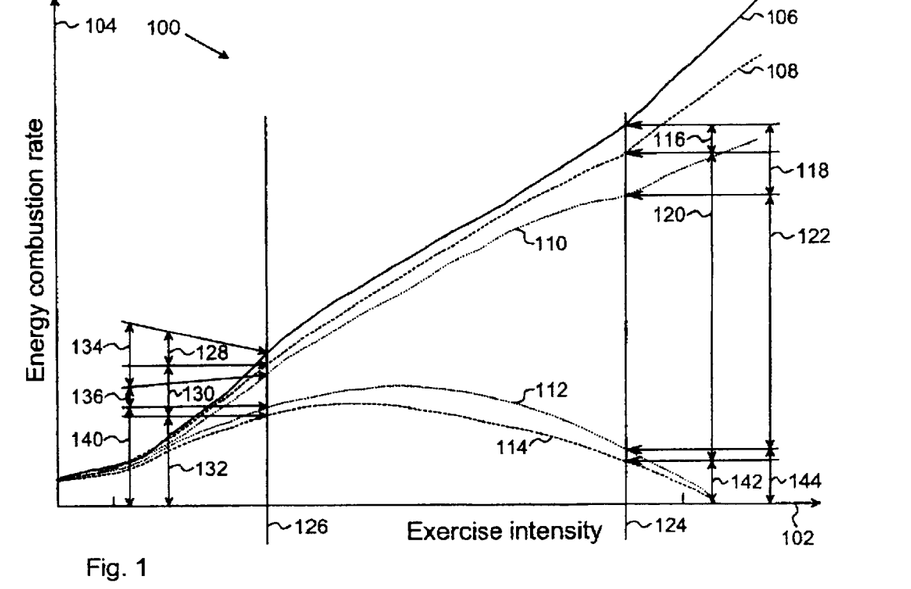
FIG. 1 is a schematic representation of a utilization of energy substrates in various carbohydrate reserves states.

With reference to FIG. 1, let us consider a group 100 of energy combustion curves 106, 108, 110, 112, 114 illustrating how a person's different energy substrates, such as fat, carbohydrates, and proteins are utilized at different carbohydrate reserve situations and exercise intensities. The x axis 102 shows exercise intensity in arbitrary units, while the y axis 104 illustrates energy combustion rate in Kcal/min units, for example. The dashed curves 108, 114 represent a case where the carbohydrate reserves are high. Such an exercise stage may be the beginning of the exercise and when the person's nutrition stage is stable. The dotted curves 110, 112 illustrate a case where the carbohydrate reserves are low. The solid curve 106 shows total energy combustion rate as a function of the exercise intensity. The energy combustion may also be referred to as energy expenditure.

A carbohydrate reserve characterizes the amount of carbohydrates available for energy combustion in the person's body.

Curves 108, 110 represent the summed combustion rate of carbohydrates and fat. Curves 112, 114 represent the fat combustion rate. Thus, the carbohydrate combustion rate at an arbitrary exercise intensity and/or carbohydrate reserve situation may be obtained by subtracting fat combustion values from values of curves 108, 110. Correspondingly, the protein combustion rate at an arbitrary exercise intensity and/or carbohydrate reserve situation may be obtained by subtracting the summed carbohydrate and fat combustion rates, i.e. values of curves 108, 110, from the values of the total energy combustion curve 100. The use of the combination of the curves depends on what curves are available and energy substrate combustion is to be determined.

In order to illustrate the physiological background of the invention, the energy combustion distribution between the energy substrates are considered in a low intensity point 126 and a high intensity point 124.

Energy gaps 116, 128 represent the protein combustion rate in the case of high carbohydrate reserves, while energy gaps 118, 134 represent protein combustion rate in the case of low carbohydrate reserves. Energy gaps 120, 130 represent the carbohydrate combustion rate in the case the carbohydrate reserves are high, while energy gaps 122, 136 show the carbohydrate combustion rate when the carbohydrate reserves are low. Energy gaps 132, 142 illustrate the fat combustion rate when the carbohydrate reserves are high, whereas energy gaps 140, 144 show the fat combustion rate when the carbohydrate reserves are low.

FIG. 1 shows that the protein combustion rate is low when the carbohydrate reserves are high, or the exercise intensity is low or moderate. However, when the carbohydrate reserves get depleted, the total protein consumption rate becomes significant. This is especially the case with high exercise intensities i.e. the total energy combustion rate increases.

FIG. 1 also illustrates that the contribution of each energy substrate to the total energy consumption changes as a function of exercise intensity and the exercise history. The consideration of the exercise history may be returned to the exercise intensity when the exercise intensity is considered in time.

In an embodiment of the invention, the fat combustion curves 112, 114 are parametrized and/or stored in a look-up table, wherein the fat combustion curves 112, 114 correspond to various exercise intensity levels and carbohydrate reserve situations. The parametrization and/or formation of the look-up tables may be based on statistical consideration of a population with the same demographics as the person under consideration.

In an embodiment of the invention, the curves 108, 110 characterizing the protein combustion rates are parametrized and/or stored in a look-up table, wherein the curves 108, 110 correspond to various exercise intensity levels and carbohydrate reserve situations. The parametrization and/or formation of the look-up tables may be based on statistical consideration of a population with the same demographics as the person under consideration.

Curves 108, 110, 112, 114 may also be represented in absolute scale and/or as percentage of the total energy combustion rate. The parametrization and/or formation of the look-up tables may be done accordingly.

The methods and apparatus according to embodiments of the invention may apply various energy combustion models which predict the energy combustion rates, such as those shown in FIG. 1. An energy combustion model may be a carbohydrate combustion model for characterizing carbohydrate combustion characteristics, a protein combustion model for characterizing protein combustion characteristics, and a fat combustion model for characterizing fat combustion characteristics. A combustion model, in general, characterizes a metabolic combustion process as a function of a person's personal characteristics, physiological and nutritional state, and a variable measurable on the person, such as cardiovascular parameters, speed, and/or activity. As a general rule, the total energy combustion rate ($E_{TOT}$) may be written as $$E_{TOT} = E_{CHO} + E_{FAT} + E_{PRO} + E_{RES},\quad(1)$$

wherein $E_{CHO}$, $E_{FAT}$, $E_{PRO}$ represent the carbohydrate combustion rate, fat combustion rate, and protein combustion rate, respectively. Factor $E_{RES}$ represents a residual energy combustion component and is neglected in the following discussion. An accumulated energy combustion may be obtained by integrating the energy combustion rate with respect to time or other variable which characterizes the progress of the exercise. The accumulated energy combustion may be calculated in this way for the total energy combustion, a combination of energy substrate combustions, such as carbohydrates and proteins, and/or for each energy substrate separately.

The total energy combustion rate may be obtained from intensity information, such as heart rate information. Personal characteristics, such as demographics and the person's performance capacity, i.e. maximum oxygen uptake, and activity information may be taken into account in the determination of the total energy combustion rate. A model for obtaining the total energy combustion is described in detail in U.S. Pat. No. 6,537,227 to Kinnunen, which is herein incorporated by reference.

In an embodiment of the invention, the carbohydrate combustion model considers carbohydrate combustion rate as a function of total energy combustion rate, the fat combustion rate, and the protein combustion rate. In an embodiment, the carbohydrate combustion rate may be written as $$E_{CHO^+} = E_{TOT} - E_{FAT} - E_{PRO}\quad(2)$$

The fat combustion rate may be obtained from a fat combustion model, for example, wherein the fat combustion rate is a function of heart rate variability and heart rate. Such a model is dealt with in detail in U.S. Pat. No. 6,540,686 to Heikkila, which is incorporated herein by reference in its entirety.

The protein combustion model may be expressed using instantaneous protein burning rate $E_{PRO,i}$ as $$E_{PRO,i} = E_{CHO,Ri} + E_{CHO,i}, \quad (3)$$

wherein $E_{CHO,R}$ is the carbohydrate reserve at instant i and $E_{CHO,i}$ is the carbohydrate burning rate at instant i. The carbohydrate reserve at instant i may be obtained from the carbohydrate reserve in the beginning of the observation period and accumulated carbohydrate consumption from the beginning of the observation period. The carbohydrate consumption may be obtained from the carbohydrate combustion model.

In the energy combustion models, in an embodiment of the invention, fat may be seen as an infinite deposit. However, carbohydrate stores, such as that found as glycogen in the liver and muscles, and protein used via gluconeogenesis, may be considered as depleted energy stores that need to be recovered. Using an athlete's anthropometry, exercise intensity, and accumulated energy combustion during the exercise, both carbohydrate reserve state and the state of its depletion can be determined, which leads to a prediction of the energy combustion curves 108, 110, 112, 114 of FIG. 1. By using aerobic and anaerobic thresholds, also denoted AeTh and AnTh, respectively, normal carbohydrate depletion, wasting of glucose in anaerobic glycolysis, and protein utilization via gluconeogenesis can be individually determined. When loading is performed on glycolytic intensity and carbohydrate stores are diminished, the model may assume remarkable gluconeogenesis. For example, in only one hour of heavy exercise, protein used as an energy substrate approaches ten percent of total energy used. The model described herein may assume availability and adequate consumption of energy containing drinks or food during long-lasting training sessions.

With reference to the example of FIG. 1, at the beginning of an exercise session with full carbohydrate reserves, the percentage of carbohydrate combustion rate depends on intensity and can be 10-20% of the total energy combustion rate at zero intensity, 50-70% at aerobic threshold, 85-94% at anaerobic threshold, and about 95% at maximum intensity. The percentages may depend on anthropometrics, such as gender and body mass index (BMI). The percentage can be interpolated between intensity thresholds.

The fraction of energy obtained from protein combustion may be, for example, about 0-1% at zero intensity, about 1-2% at aerobic threshold, 2-4% at anaerobic threshold, and 3-6% at maximum intensity. Conversely, when carbohydrate stores become more and more depleted, the role of protein as an energy substrate becomes much more important. When carbohydrate stores become more depleted, it requires more effort to maintain the intensity above aerobic threshold, and finally it becomes impossible. The fraction of energy derived from protein increases at all intensities, and may represent about 10% at zero intensity, about 20-30% at aerobic threshold, about 70% at anaerobic threshold, and close to 100% at maximum intensity. The final two values being theoretical since the human body will refuse to exercise at such a high intensity after carbohydrate stores are close to depletion.

The exercise intensity is typically a measurable variable which may be measured with a sensor of the apparatus. Such measurable variables include heart rate, running/cycling speed, speed related to individualized parameters (such as maximum speed, threshold speed) or internal temperature. Furthermore, the following parameters may be used:

(1) one or more heart rate parameters, such as resting heart rate, maximum heart rate, aerobic threshold, and anaerobic threshold;

(2) information concerning the user's individual characteristics, such as age, height, weight, gender, fitness ($VO_{2max}$ and/or alternative performance parameters); and (3) a description of the sport or exercise that the user is engaged in if a mechanical strain model is used (alternatively, this information may be determined automatically from heart rate dynamics or other sensors that can optionally be included, such as an accelerometer).

The apparatus and method in accordance with the present application may process the following parameters:

(1) total volume of the user's carbohydrate reserves;
(2) metabolic substrate use (fat, carbohydrate, and/or protein) depending on exercise intensity and amount of carbohydrate storage remaining;
(3) nutritional intake taken in prolonged exercise sessions;
(4) relationship of intensity to mechanical stimulus, which depends on the cumulative mechanical stimulus, wherein mechanical fatigue adds to the effect of subsequent mechanical stimulus; and
(5) total amount of mechanical strain is calculated based on heart rate, individual heart rate parameters, and the sport and/or exercise the user is engaged in.

The apparatus and method in accordance with the present application may provide the following outputs:

(1) training load, which is based on metabolic fatigue and/or energy depletion;
(2) mechanical stimulus, which is based on neuromuscular and/or biomechanical fatigue; and
(3) recovery condition as a function of time, in which the total recovery duration is equal to the recovery time needed.

The parameters processed or outputs listed above may be displayed on portable devices, such as a wrist unit or computer display. These values can also be stored, accessed, or shown on-line during exercise and/or the rest or recovery period, or summary values may be provided following the exercise session. Training load or recovery time values can be summed over a period of time, such as a week, and these values may be associated with individual or general limits to evaluate in terms of optimal training conditions.

The apparatus and method in accordance with the present application provides the following benefits:

(1) technical benefits include user attractive parameters that can be calculated based on existing and user-friendly measurement technology.
(2) commercial benefits including the following:
   (a) application of improved performance capacity, training load, and recovery time parameters, which are targeted for individual users, improvement of the same parameters when evaluating tolerance to repeated strenuous sessions in special work-related tasks, such as that endured by soldiers, firemen, and asphalt workers;
   (b) use of an advanced model of anaerobic fatigue;
   (c) improved motivation for the acquisition of a heart rate monitor by promising a better balance between training and recovery periods, and preventing muscular pain while achieving a maximum tolerable training stimulus;
   (d) improved satisfaction of user requirements including (i) meeting the needs of athletes and ordinary users to recognize or foresee the most appropriate time for the next training session, since adequate recovery after training sessions is a prerequisite for improved performance; (ii) overcoming issues caused by the several subjective factors that make it impossible to analyze momentary recovery status reliably; (iii) making it easier to determine peak performance at a desired time by comparing different training sessions or weekly training volumes with respect to recovery time; and (iv) shortening recovery time, decreasing muscular pain, and increasing additional quality training time by providing feedback to the user concerning accumulated mechanical stimulus in the current training session, since muscular pain after exercise is normally an unexpected and unwanted factor that is related to certain pain causing phenomena during exercise.

The apparatus and method in accordance with the present application can be used to evaluate when it would be a suitable time for the next training session. Thus, it can be used to plan optimal training sessions with respect to intensity, duration, and training modality in view of upcoming competitions or training sessions. For example, the user can plan a training session that depletes carbohydrate stores to a desired level. The apparatus and method can also be used to compare different training regimens that have taken place to determine optimal weekly training volume for performance improvement. Nutritional requirements for recovery sessions can be achieved with improved accuracy. The user can stop a training session at the appropriate time to keep muscle soreness in control and still continue long enough to achieve a desired training load. Training modality can be determined from heart rate dynamics and/or derivatives thereof. Modality can be, for example, continuous, intermittent, and/or strength training, as well as various sports and/or activities.

The apparatus and method in accordance with the present application define a mathematical model to refine exercise intensity information into training load which may be presented with a parameter and which makes different exercise sessions comparable in terms of adaptive or exhausting characteristics. In addition to training load, an athlete needs an understanding of his or her recovery needs and the optimum time window for subsequent exercise sessions. To derive a measure of post-exercise recovery time, a model is defined herein to determine recovery time using input information, such as exercise intensity, user characteristics, and exercise mode. These two novel parameters, training load and recovery time, can be presented together to form a comprehensive visualization of training stress and its consequences on the user's training schedule and need for rest. Both training load and recovery time allow the athlete and/or coach to plan and analyze a training schedule using software executed by a computing device.

Training load which is the measure of adaptive stimulus and fatigue caused by a single training session, is a value typically ranging from 50 to 200 in arbitrary units. The arbitrary unit may be m(CHO)/(m(person)*t), wherein m(CHO) is the amount of carbohydrates, m(person) is mass of a person, and t is time. Thus, the training load may be expressed in terms of carbohydrate reserve debt in time units scaled with the person's size. Training load reflects the non-fat energy cost of exercise. Thus, in an embodiment of the invention, the training load may be proportional to accumulated energy combustion of carbohydrates and proteins as follows:

$$TL = A(E_{CHO,ACCU} + E_{PRO,ACCU}), \quad (4)$$

wherein A is a scaling factor that may depend on user characteristics, such as age and gender.

In an embodiment of the invention, the training load is proportional to the total accumulated energy combustion and accumulated fat combustion as follows:

$$TL = B(E_{TOT,ACCU} - E_{FAT,ACCU}), \quad (5)$$

wherein B is a scaling factor which may depend on user characteristics, such as age and gender.

In general, the training load may be expressed as $$TL = TL(I, W, F, G, A, HR_{rest}, HR_{max}, AerTh, AnTh, Im, Ad), \quad (6)$$

wherein I, is the exercise intensity, W is the person's weight, F is the person's fitness level, G is the person's gender, A is the person's age, $HR_{rest}$ is the person's rest heart, $HR_{max}$ is the person's maximum heart rate, AerTh is the person's aerobic threshold, AnTh is the person's anaerobic threshold, Im is the modality of the exercise, and Ad is the person's adaptiveness to the exercise.

One of the benefits of the training load parameter is that it renders different exercises comparable to each other. As such, training load allows the coach or athlete to adjust exercise intensity and duration to meet daily and weekly targets. Continuous monitoring of training with training load will help the athlete to recognize his or her personal limits and the correct amount of loading in daily or weekly basis.

Figure 2:
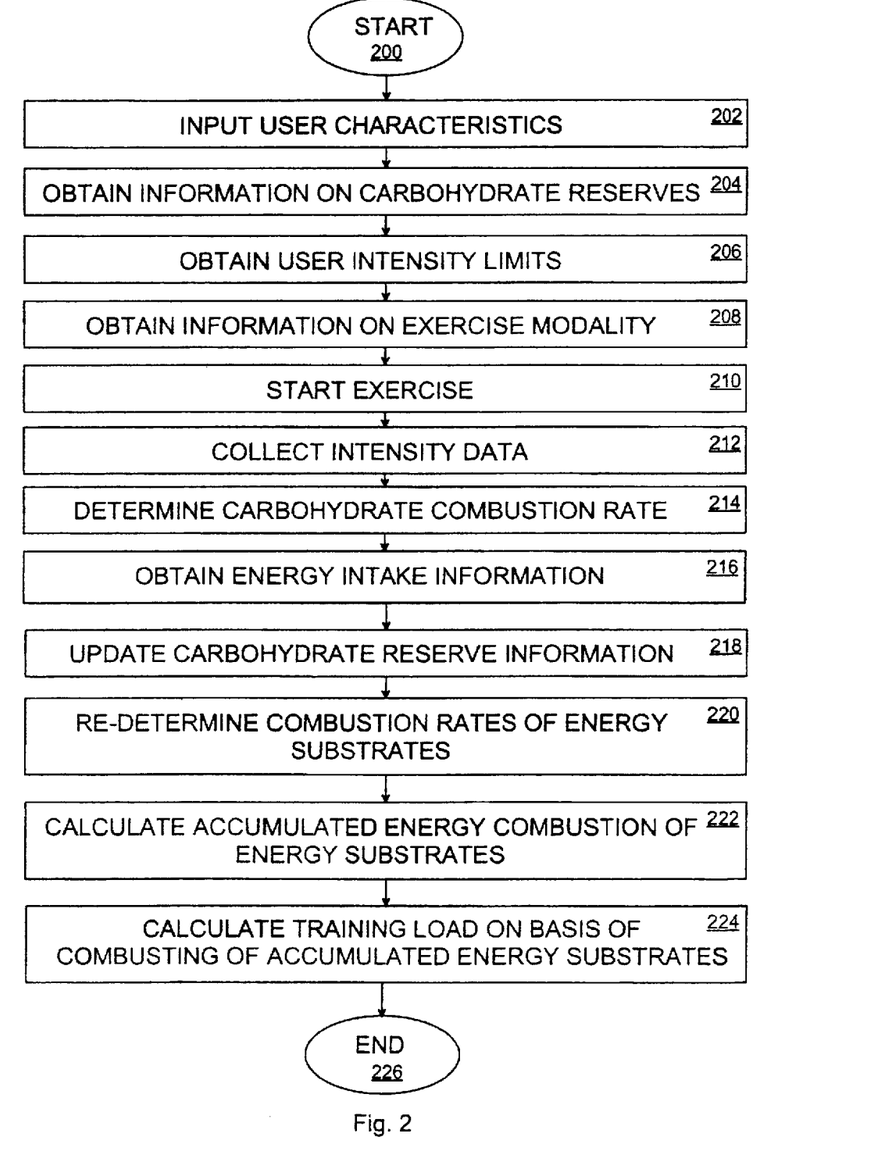
FIG. 2 is a flowchart of a method in accordance with the present application concerning the training load.

FIG. 2 shows a flowchart of a method for determining training load.

In 200, the method is started.

In 202, user characteristics or anthropometrics are input or determined. User information includes age, body height, body weight, and gender. If the user's fitness level or performance capacity is known, this value can be input in 202. Alternatively, the fitness level may be estimated or calculated based on the user characteristics or anthropometrics. The fitness level or performance capacity may be expressed with the maximum oxygen uptake capability, for example.

In 204, the amount of carbohydrates in the body is obtained by inputting, calculating or estimating based on gender, body weight, and fitness level, for example. In an embodiment of the invention, recovery status following a prior exercise session is taken into account in this determination.

In 206, individual or user intensity limits are input or determined. In the case of heart rate, the user intensity limits include resting heart rate, maximum heart rate, metabolic threshold heart rates, aerobic threshold, and anaerobic threshold. If these values are not known, they can be estimated from user characteristics defined in 202, especially age and fitness level. Typical values for metabolic threshold levels are 70-80% $HR_{max}$ for a first threshold, and 85-95% HRmax for a second threshold.

In 208, the modality of the exercise is obtained. Individual intensity limits determined in 206 may depend on exercise modality, such as intermittent, continuous, strength, swimming, cycling, running, or skiing, since the amount of muscles used and posture affect the relation of heart rate and/or internal temperature to metabolic intensity, and the speed to metabolic intensity relation may depend strongly on the exercise mode or modality.

In 210, the exercise is started. The process begins in response to the user pressing a button to start the exercise mode. Alternatively, when the measured intensity exceeds an intensity threshold, an exercise session may be automatically started.

In 212, intensity data, such as heart rate data, is collected. Running, cycling, or other sports mode speeds may be detected with a modality appropriate speed sensor, such as an inertia detector, GPS, cadence detector, or its equivalent.

In 214, the carbohydrate combustion rate is determined on the basis of the intensity data. A carbohydrate combustion model may be used. In accordance with the present application, the fractions of each energy substrate, such as fat, carbohydrate, and protein changes dynamically according to the amount of carbohydrate stores remaining in the user's body.

The percentage of carbohydrate oxidation is adjusted in step 220 according to the amount of carbohydrates left in the body as determined in step 218.

In 216, information on carbohydrate intake is obtained. In long-lasting exercise sessions, such as a team sports event or marathon run, sports drinks and other energy sources are available for athletes. In exercise sessions lasting even longer than that, such as adventure sports, food containing protein is typically available and ingested by athletes. A certain amount of energy expended during exercise is obtained directly from food eaten during exercise, thus sparing energy substrate stores in the user's body. The amount of ingested food can be input to the method and apparatus in accordance with the present application or it can be estimated by other means. Alternatively, it can be assumed that a certain fraction of the energy substrates (carbohydrate, protein, fat) recovered in a predefined time window immediately following exercise is received from food ingested during the exercise session. This fraction can be, for example, 70-100% as indicated in the description of the recovery time calculation and FIG. 3 herein. If intensity becomes very low, and intensity recording is not stopped, this block is needed since energy stores can be filled rather than used during recovery periods that are long enough.

In 218, the information on carbohydrate reserves in the body is updated. This may be done by using the initial amount of carbohydrates in the user's body, the carbohydrate combustion rate, and the information concerning carbohydrate/protein intake.

In 220, the protein, fat, and carbohydrate combustion rates are re-determined corresponding to the prevailing carbohydrate reserves.

In 222, the accumulated energy combustion of energy substrates is calculated. In an embodiment of the invention, accumulated protein and carbohydrate combustion are calculated.

In 224, training load is calculated on the basis of the accumulated energy substrates. In an embodiment of the invention, the training load is calculated on the basis of accumulated protein and carbohydrate combustion.

In 226, the method ends.

In an embodiment of the application, the summary information is displayed to the user before the end of the method. Summary information may include the amount of carbohydrates, protein, and fat consumed, and training load information, which can include a combination of carbohydrates and protein. Also or alternatively, the training load information may be stored into the memory of the apparatus for later use.

The method of training load determination may be implemented using software executed in a digital processor of an apparatus, such as a mobile phone, a sport computer, a circuit board, exercise equipment, wrist device, heart rate transmitter, or a base station.

Recovery instructions can also be provided at this step.

Mechanical stimulus is a category of training load that characterizes the effect of an exercise on muscles.

Figure 3:
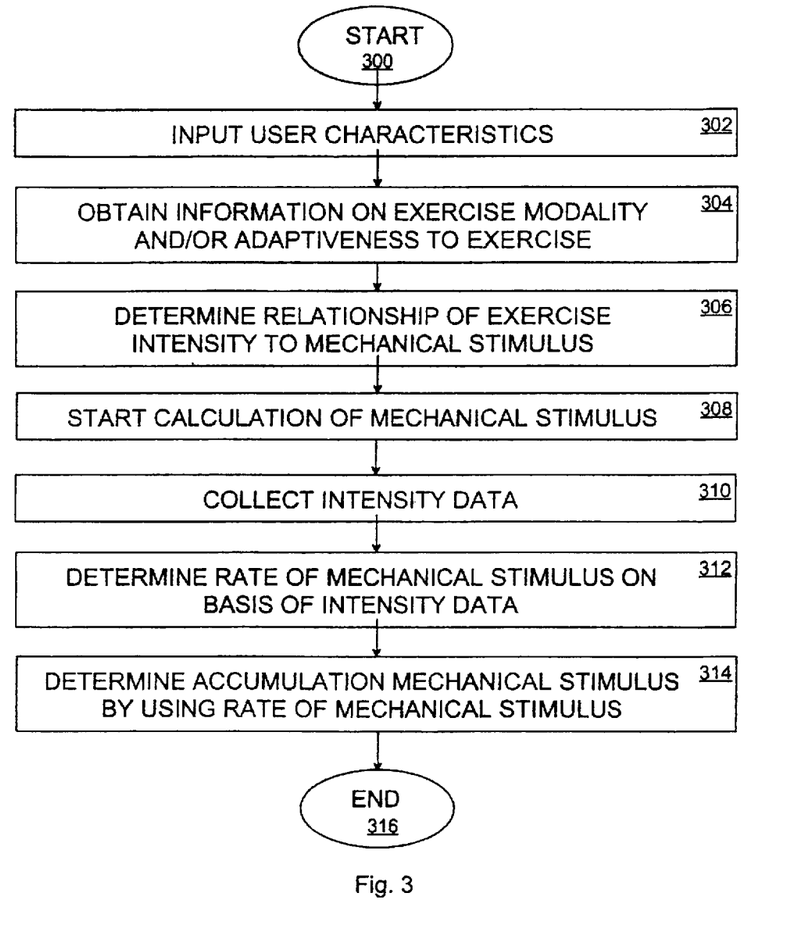
FIG. 3 is a flowchart of a method in accordance with the present application concerning an accumulated mechanical stimulus or impact.

FIG. 3 shows a flowchart of a method in accordance with the present application concerning the determination of mechanical stimulus that will now be described.

In 300, the method starts.

In 302, user characteristics or anthropometrics are input or determined. Information may include age, body height, body weight, and gender. If the user's fitness level or performance capacity is known, this value can be used in this step. Alternatively, fitness level may be estimated based on user characteristics or anthropometrics.

In 304, exercise modality is obtained by inputting or determining. The exercise modality can be divided into categories, such as continuous, intermittent and strength training. In addition, more detailed categories can be used, or an exercise-mode-specific impact factor can be defined. To a certain extent, the exercise modality may be detected automatically from heart rate dynamics if the training type is continuous or intermittent. For example, fast and regularly repeating changes in the heart rate over time represent an intermittent training modality or strength training. Accelerometers attached to the wrist or body may also be used to determine this information, or the sports type may be input by the user. The user's familiarity to the current training modality is also input or determined in step 304, such as a value from one to ten representing predefined levels of familiarity.

In 306, the relationship of exercise intensity to mechanical stimulus is determined by using the exercise modality and adaptiveness to the exercise, for example. The mechanical stimulus may be characterized, for example, by heart rate information obtained during the exercise. A greater heart rate indicates a greater mechanical stimulus. At low intensities, such as when the heart rate is below 50% $HR_{max}$, mechanical stimulus is practically zero. At maximum intensity, such as when the heart rate is at $HR_{max}$, the rate of mechanical stimulus is at the user's maximum levels. The mechanical stimulus may be represented with arbitrary units proportional to the number of repetitions, time, or the load, such as force. The relationship of heart rate to mechanical stimulus or biomechanical strain depends on the exercise modality or impact and the user's familiarity to the current exercise modality. The effect of exercise modality is the greatest at moderate intensity. Thus, a flexpoint is defined to represent the rate of mechanical stimulus at moderate intensity, and both flexpoint intensity and flexpoint stimulus rate may depend on the sports type or modality. For example, in continuous sports mode, such as constant speed cycling, the flexpoint intensity may be the anaerobic threshold (about 90% HRmax) and the flexpoint stimulus rate about 1 unit per time. In intermittent sports, such as ice hockey or football, the flexpoint intensity may be about 80% $HR_{max}$ and the flexpoint stimulus rate about 2 units per time. In strength training, flexpoint intensity may be about 70% $HR_{max}$ and flexpoint stimulus rate about 3 units per time. If the user is unfamiliar to the training modality, the flexpoint stimulus may be 50-100% greater and the flexpoint intensity 5-15% $HR_{max}$ lower. User anthropometrics and fitness levels may be used to adjust the intensity to mechanical stimulus relationship. For example, heavy users may have higher stimulus rates in continuous and intermittent sports modes than lighter users, the basis for which is provided in the following equation:

$$\text{Force} = \text{mass} \times (\text{initial speed} - \text{final speed})/\text{time interval} \quad (7)$$

In 308, the mechanical stimulus calculation is started. The start may be initiated as a response to the user pressing a button to initiate the exercise mode. Alternatively, when measured intensity exceeds an intensity threshold, the exercise mode may be automatically started.

In 310, intensity data is collected in step 405 at, for example, 1 to 60 second intervals for heart rate with a heart rate monitor or its equivalent, or running, cycling, or other sports mode speed with a speed sensor, inertia detector, GPS, or their equivalent.

In 312, the rate of mechanical stimulus or impact is determined on the basis of the intensity data. In an embodiment, the exercise modality and/or adaptiveness to the exercise are used in the determination of the mechanical stimulus.

In 314, the cumulative or sum of the mechanical stimulus or impact is determined on the basis of the rate of mechanical stimuli.

In an embodiment of the invention, when mechanical stimulus accumulates, it can be estimated that the biomechanical control of movement becomes worse, and the amount of mechanical stimulus or impact increases the heart rate. This increase can be about 0-30%.

In 316, the method ends. In an embodiment of the invention, summary information is displayed to the user. Summary information may include a sum of the mechanical stimulus or impact, the relation of the mechanical stimulus to general limits tolerable for human beings, and/or its relationship to bone and muscle health. Using the recovery time calculation model described herein, the probability of delayed onset muscle pain or probable muscle pain intensity at a certain time following or during exercise can be estimated.

Recovery time may be based on training load and may have two fundamental components; a metabolic component and mechanical component.

The metabolic component increases and decreases with training load. When calculating the metabolic component of recovery time, the cumulative depletion of both carbohydrate and protein are taken into account to estimate the time needed for re-synthesis or recovery. Carbohydrate re-synthesis has non-linear characteristics that take into account glycogen molecule building, as shown in FIG. 5. Due to the lower availability of free synthesis sites in reduced glycogen molecules, the re-synthesis rate can be assumed to be lower in absolute terms. The relative rate, however, stays at the five percent level typically seen when ingesting a protein-carbohydrate mixture after exercise. This will cause certain phenomena in recovery. For example, if carbohydrate stores are seriously depleted which may be due to a long and vigorous exercise over 2000 kcal accumulated total energy combustion, the metabolic component will show remarkably delayed recovery. Progress in carbohydrate rebuilding is initially very slow but accelerates later on. After low-intensity exercise, during which remarkable fat utilization takes place, the metabolic component may show an almost linear decay, and the metabolic recovery time is short. Like fat, protein is regarded as an infinite storage. Thus, contrary to carbohydrate recovery, it is difficult to determine how protein stores are refilled after exercise. However, vigorous use of protein as energy causes overall catabolic and anti-immunologic consequences that must be reversed. As a result, a recovery component that is small in magnitude but long in duration will be summed to the carbohydrate component. The protein recovery component has the same duration as elevated post-exercise gastrointernal and cellular protein intake and has the same risk to upper respiratory tract inflammation.

Figure 4:
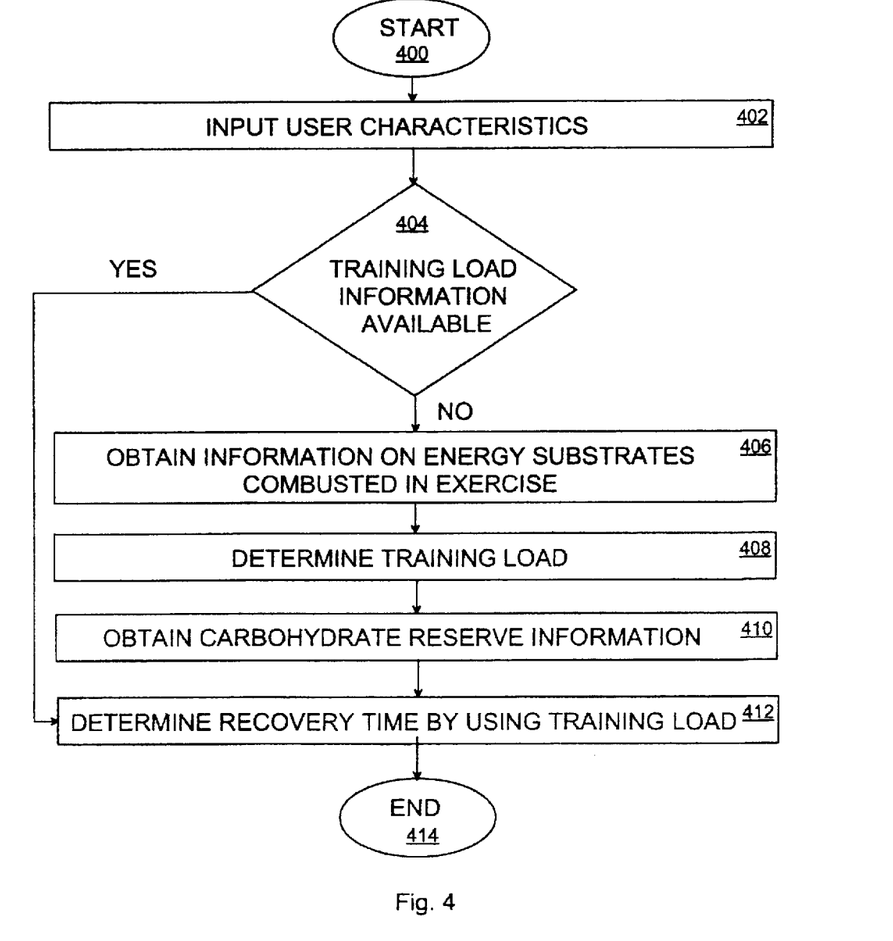
FIG. 4 is a flowchart of a method in accordance with the present application concerning recovery characteristics.

The mechanical recovery component is due to muscular-pain and inflammation and contributes to the recovery time. This phenomenon is called delayed onset muscle soreness (DOMS). DOMS has a well-defined occurrence and temporal manifestation. In order to determine DOMS from exercise intensity, such as heart rate dynamics, the athlete may define the impact of the performed exercise (low-impact-high impact-strength training) and the state of his familiarity with this particular mode of training. It can be assumed that mechanically highly loading epochs manifest themselves simultaneously with a measurable variable, such as cardiovascular strain. Depending on the exercise mode, heart rate dynamics may be weighted to meet correct mechanically induced post-exercise load or tissue rupture. The cumulative value of mechanical load is transformed into a temporal manifestation of DOMS. Being a mathematically continuous function, DOMS may be defined to peak between 24 to 48 hours after exercise as shown in FIG. 4. Once the mechanical load threshold is exceeded, the inflammation will occur within this time window. Increasing cumulative mechanical load delays the occurrence of modelled DOMS peak and increases the magnitude thereof, which is scaled comparable to perceived post-exercise fatigue.

In the model in accordance with the present application, the muscular inflammation component is most pronounced when the exercise modality is strength training. However, a fully developed, high DOMS may also be seen when the mode of training is low impact with, for example, running. If an athlete has undergone a long-lasting fatiguing period and is still experiencing high intensity, significant tissue damage can be assumed to occur. When the intensity (speed) is high enough, exhaustion may ruin several reflexes, such as stretch-shortening cycle, neuromuscular control of landing-phase, and subsequent take-off. Thus, impacts generated by high speed are poorly tolerated and muscles and tendons are exposed to eccentric action.

In accordance with the method and apparatus of the present application, while training load is a one-parameter quantity, recovery time represents two recovery components, a metabolic recovery component and a mechanical component. The metabolic component and training load are commonly derived from exercise heart rate. In addition to calculations for determining training load and the metabolic recovery component, exercise modality and the familiarity of the athlete to the current exercise modality are utilized to quantify a muscular pain component, which includes connective tissue and muscular inflammation. In the present model, strong muscular pain is also linked to delayed metabolic recovery. Training load increases exponentially as temporal training intensity increases, and is based on individually calibrated energy metabolism modelling. This basis allows training load to serve as a cornerstone for further recovery time calculation utilizing the metabolic recovery component of training load.

Physical loading leads to a disturbance in bodily homeostasis inducing several biological mechanisms that take place during recovery periods, such as stress reaction, catabolism, anabolism, and tissue recovery. Recovery adapts the athlete to better tolerate the same type of loading in the future. Visual analysis of a heart rate curve or energy expenditure during training is not an easily interpretable way to determine the capability of a training session to disturb homeostasis.

FIG. 4 shows a flowchart of method for determining recovery time, as will now be described.

In 400, the methods starts.

In 402, user characteristics are obtained.

In 404, it is deduced whether or not training load information is available. The training load information obtained in 406 may comprise the metabolic training load value and/or a mechanical training load value.

If the training load information is not available, information on the accumulated energy substrates combusted in one or more previous exercises is obtained. In an embodiment of the invention, the information on the accumulated energy substrates comprises: information on accumulated total energy combustion in one or more previous exercises; information on accumulated protein combustion in one or more previous exercises; and/or information on accumulated fat combustion in one or more previous exercises.

The information on the accumulated energy substrates listed above may be input to the apparatus by the user or an external apparatus.

In 408, the training load is determined. In an embodiment of the invention, method described in conjunction with FIGS. 2 and/or 3 is applied for determining the training load.

In 410, information on carbohydrate reserves in the person's body are obtained.

In 412, the recovery time is determined on the basis of the training load. The training load may be considered as a debt that needs to be repaid, wherein recovery time is the duration of time required to repay that debt. Different rates of debt repayment or recovery may be used for each component of training load. The rate may also change according to the amount of recovery needed and/or energy currently stored in the user's body. The speed of one component may depend on the amount of one or more additional components. For example, if there is a high mechanical training load, the speed of carbohydrate recovery may slow down. Also, the user's long term activity level or fitness level may affect duration of the recovery time. For example, a user that is accustomed to high training volumes is able to recover faster.

In an embodiment of the invention, the recovery time determination applies a model for reloading carbohydrate reserves. A model for reloading carbohydrate stores comprises a relationship between the speed of reloading the carbohydrate stores and the prevailing carbohydrate stores, and the availability of carbohydrates. In an embodiment of the invention, the carbohydrate recovery time is inversely proportional to the prevailing carbohydrate stores when the carbohydrate stores are less than a predefined threshold. For example, if carbohydrate stores are low, carbohydrate recovery speed can be slower than when stores are moderately full. When carbohydrate stores are almost full, the recovery speed may slow down again.

In an embodiment of the invention, the recovery time determination applies a model for reloading protein catabolism. Catabolism is the set of metabolic pathways that break down molecules into smaller units and release energy. The recovery speed for overcoming protein catabolism may change dynamically depending on recovery need. This component may be dependent on the level of resting metabolism, protein intake, the user's long term activity level, as well as other factors In an embodiment of the invention, the recovery time determination applies a model for recovering from mechanical trauma or neuromuscular fatigue. The model for recovering from mechanical trauma or neuromuscular fatigue characterizes the person's ability to recover from the mechanical stimulus. Increasing the amount of mechanical training load may increase the intensity of muscle pain, mechanical trauma, and/or the need for neuromuscular recovery and delay its peaking time.

In an embodiment of the invention, the model for recovering from mechanical trauma or neuromuscular fatigue comprises formulation of an initially increasing and then decreasing function, and then changes both time intervals and the values derived by these function in accordance with the mechanical training load. The form of the recovery function may be as a vector $$A = [0,1,2,4,8,16,32,40,40,34,20,10,5,0], \quad (8)$$

wherein each element characterizes the state of recovery from mechanical trauma at a time point. Each of the elements in the vector can be multiplied by a value that depends on the mechanical training load, which is typically a non-linear function that initially increases slowly, then increases quickly, and finally saturates. The time interval between vector elements may also depend linearly or non-linearly on the mechanical training load so that the time scale depends upon the mechanical training load.

In 414, the method of determining the recovery time ends.

In an embodiment of the invention, the results of the recovery time determination are provided or displayed to the user and may include the current recovery condition or recovery time in different combinations of different debts. For example, the results may show each component separately, the sum of different components (different recovery needs), or the maximum of different components at specific times.

With reference to FIGS. 5a to 5d, the relationship between the training load and recovery time are illustrated. The x axis 502 shows the recovery time, while the y axis 504 shows training load and/or recovery state. The person is male, 26 yrs old, 75 kg, $VO_{2max}$ is 55 ml/kg/min, $HR_{sit}$ 60, and $HR_{max}$ 198 bpm. For example, FIGS. 5a to 5d illustrate training load and its decay as a function of time. Once the training load has been generated, the recovery state can be illustrated as a residual of the training load.

Figure 5A:
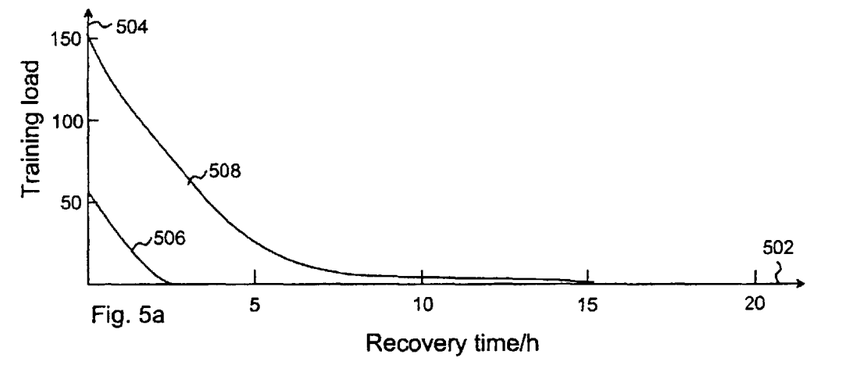
FIG. 5a is a first graph presenting the relation between training load and recovery time according to an embodiment of the invention.

FIG. 5a illustrates how the training load and the resulting recovery time depend upon the exercise intensity with a fixed exercise duration of 60 minutes. Curve 506 shows a training load (TL=62) and corresponding recovery characteristics when the exercise is light with an average heart rate of 129 BPM (beats per minute). Curve 508 shows the training load (TL=154) and the corresponding recovery characteristics when the exercise is heavy with an average heart rate of 164 BPM. The curves 506 and 508 show the drastic effect of the training load on the recovery time.

Figure 5B:
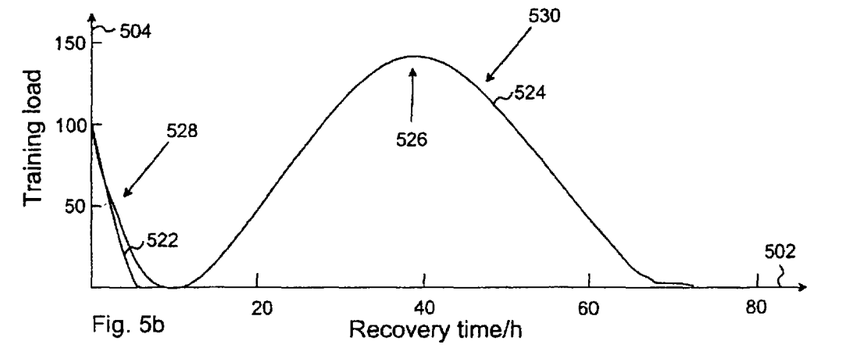
FIG. 5b is a second graph presenting the relation between training load and recovery time according to an embodiment of the invention.

FIG. 5b illustrates the effect of exercise modality on recovery time, which in this case is primarily due to mechanical training load, i.e. the muscular pain and inflammation component. The duration of the exercise is 60 minutes, and the average heart rate is 148 BPM for both curves 522 and 524. However, curve 522 represents recovery characteristics after continuous or low impact training with a training load of 103. In this case, a total recovery takes place in 5 hours. Curve 524 represents recovery characteristics after strength training or activity including eccentric actions, such as ballistic exercises. In this case, the training load is 112. The metabolic component 528, i.e. the protein and carbohydrate reload, starts immediately after the exercise, but the symptoms of the mechanical trauma, i.e. the inflammation and muscle pains are, not effective. After 24 to 48 hours, for example, the muscle pain/inflammation component 530 peaks and then decays. It should be noted that the form of the curve 524 may be based on the use of vector A provided above.

Figure 5C:
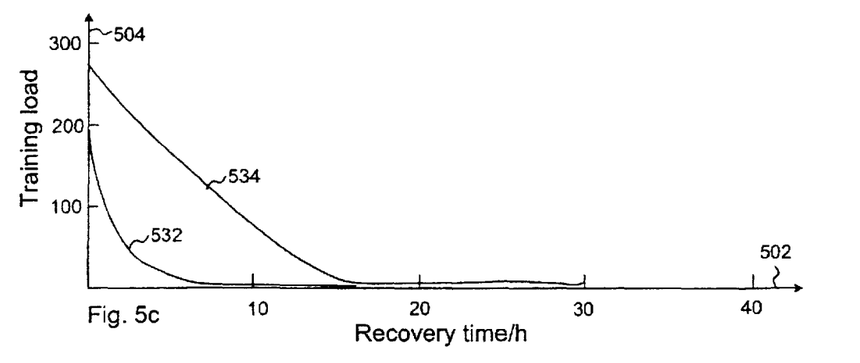
FIG. 5c is a third graph presenting the relation between training load and recovery time according to an embodiment of the invention.

FIG. 5c illustrates the effect of exercise duration on training load and recovery time. Curve 522 represents a case where the duration of a running exercise is 120 minutes while the training load is 187. Curve 534 shows a case where the running exercise duration is 180 minutes with a training load of 264. The average heart rate is the same in both of these examples. Both curves show a slow metabolic recovery and low post-exercise DOMS. In particular, curve 534 shows a very slow recovery time due to three hours of running.

Figure 5D:
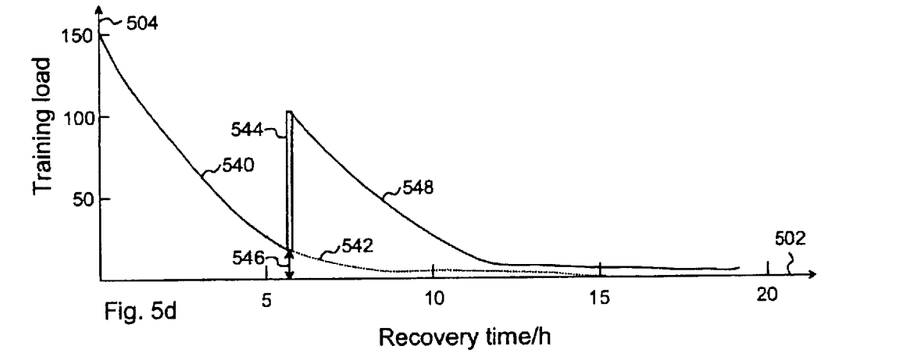
FIG. 5d is another graph presenting the relation between training load and recovery time according to an embodiment of the invention.

With reference to FIG. 5d, a case is shown where the training load and the corresponding recovery time are due to multiple exercises. Curve 540 shows recovery characteristics from a previous exercise. The dotted portion 542 shows what the recovery would have been if the recovery had been continued. However, during the recovery period, new training load 544 is introduced due to a new exercise. As a result, a new recovery curve 548 is introduced that includes an effect of the residual training load 546 associated with the previous exercise and the contribution from the subsequent exercise.

In weekly training, training load around 1000 represents an optimally developed weekly stimulus. Athletes that are accustomed to heavy training volumes and/or train for temporary overreaching, may almost double their normal weekly training load. As seen in the recovery time curves, athletes should be careful regarding the selection of exercises with respect to timing and intensity to ensure adequate recovery time and conditions.

The benefits of having access to recovery time is evident when planning a weekly exercise program, particularly that of a professional team or top endurance athlete, which is not a straightforward task, especially during the high-volume season. Along with mastering weekly total volumes, single session timing should be designed in close interaction with recently executed and forthcoming exercises. Competitive performance may be ruined with an exhaustive training session too close to a main event. Also, correct temporal management of two or more exercise sessions close to each other is critical whenever multiple sessions (such as morning, noon, and evening sessions) are incorporated, especially when high intensity training is included in the program.

Learning from the exercise history of single sessions and their consequences on recovery time, or predicting the recovery time of future sessions enables the coach and athlete to control the total workload and to optimize the timetable of the training program. When using recovery time to manage exercise programs, recovery time represents the minimum time needed to reverse the decrease in stress and performance. If super-compensation is sought following a temporary overreaching, the athlete should mildly exceed the recovery time value before the next training session, at least after the most important training session of the week. The additional recovery time needed depends on recovery conditions and may differ between individuals.

Figure 6:
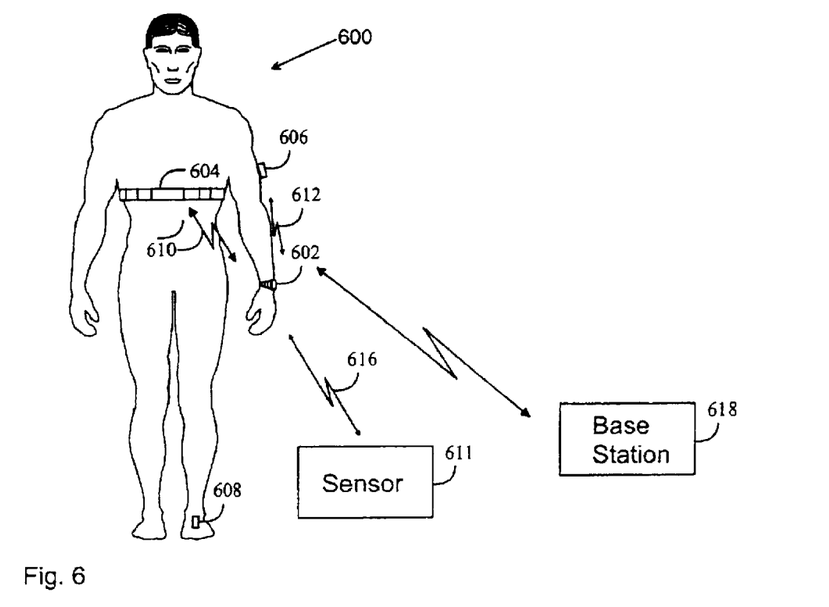
FIG. 6 is a first block diagram of an apparatus in accordance with the present application.

FIG. 6 shows an embodiment of an apparatus in accordance with the present application, in which the apparatus includes a main unit 602 and at least one peripheral device 604, 606, 608, 611 that provides information characterizing the user 600 and transmits that information wirelessly by means of a data transmission signal 610, 612, 614, 616 to the main unit 602.

The data transmission signal 610 to 616 is an electromagnetic signal, for example. In an embodiment, the frequency of the electromagnetic data transmission signal 610 to 616 is 5 kHz. In another embodiment, the frequency of the electromagnetic data transmission signal 610 to 616 is 2.4 GHz. The above solution is not, however, restricted to these frequencies of the electromagnetic signal, but the frequency may be selected freely according to the embodiment and/or external restrictions. It is typical of the apparatus that the actual user 600 monitors the apparatus and gives the necessary operational commands to the apparatus.

The peripheral device 604, 606, 608, 611 is typically an electronic device, which characterizes the user 600 and transmits the information wirelessly to the main unit 602. The information is typically information depending on performance, whereby its property characterizing the performance may be formed by combining the information with some other information characterizing the performance. An example is a peripheral device, which is attached to the training environment, such as a running track, and from which the main unit 602 receives an indicator signal when the main unit 602 enters the proximity of the peripheral device. Thus, the indicator signal implicitly contains position information characterizing the exercise, which may be combined with other exercise-related information, such as heart rate information.

In an embodiment, the peripheral device 604 is an ECG transmitter (ECG, electrocardiogram), which registers the electrocardiogram of the user 600 and transmits performance information by means of the data transmission signal 610. Thus, the performance information typically includes part of the electrocardiogram of the user 600 and parameters characterizing the electrocardiogram.

In an embodiment, the peripheral device 606 is a positioning device, such as a GPS positioning device (Global Positioning System), which transmits performance information by means of the data transmission signal 612, the information including, for example, the location, speed and/or height position of the user 600. In addition, the information may include the distance the user 600 has traveled, as well as his route and/or direction.

In an embodiment, the peripheral device 608 is a movement sensor, which transmits the information by means of the data transmission signal 614. In this case, the performance information includes movement information on the user 600, such as speed and/or acceleration. The movement sensor may be a shoe sensor, which may be connected or integrated into a shoe of the user 600. In an embodiment, the shoe sensor is a running sensor.

In an embodiment, the peripheral device 611 is a measuring device, which is used in connection with a training means, such as a bicycle and/or alternative exercise apparatus, and which measures parameters of the performance to be carried out by means of the training means, such as training force, training power, training speed or other physical variables, and transmits the parameters to the main unit 602.

The peripheral device 604 to 611 is not restricted to the above-mentioned examples, but the peripheral device 604 to 611 may be any electronic device characterizing the performance and transmitting performance information wirelessly to the main unit 602. The main unit 602 receives the data transmission signal 610 to 616 and processes the performance information. Processing may include digital processing of the performance information by means of calculation algorithms, storage of the performance information, definition of the parameters describing the performance, and displaying the parameter values describing the performance to the user. Parameters describing the performance may include heart rate parameters, energy variables, user speed, and/or user activity. The main unit 602 typically includes a receiver for receiving the data transmission signal 610 to 616, a digital processor for processing the performance information, a memory for storing training-related data and coded instructions to perform the methods in accordance with the present application, and a user interface for displaying the information to the user 600 and inputting commands to the apparatus. In an embodiment, the main unit 602 includes a transmitter for transmitting the data transmission signals to the peripheral device 604 to 611.

In an embodiment, the main unit 602 is a wrist device to be fastened to the wrist of the user.

In another embodiment, the main unit 602 is provided with a quick adapter, by means of which the main unit 602 may be fixed to a desired location, such as a bicycle, structure of an exercise apparatus, and/or socket placed on the user's body.

In an embodiment, the main unit 602 is integrated in connection with the peripheral device, such as an ECG transmitter belt to be fixed around the chest. In this case, the main unit 602 does not necessarily have a user interface, which may be replaced by means of a separate server by using a wireless data transmission connection between the server and the main unit 602.

A base station 618 may be implemented and configured to receive and process information from one more main unit 602 and/or the peripheral devices 604 to 611 associated with one or more users in accordance with the methods of the present application.

Figure 7:
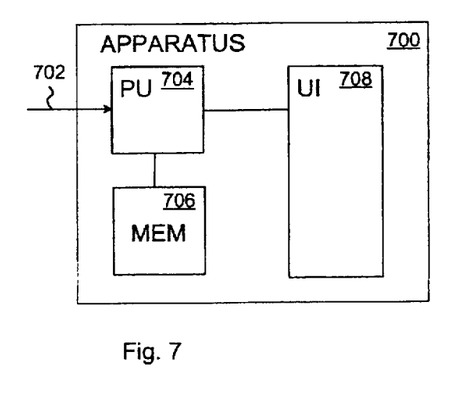
FIG. 7 is a second block diagram of an apparatus in accordance with the present application.

An example of an apparatus 700 according to the invention is shown in FIG. 7. The apparatus may be applied to implement the method of determining the training load, mechanical stimulus, and/or the recovery time. FIG. 7 shows a processing unit (PU) 704, a memory unit (MEM) 706 connected to the processing unit 704, and a user interface (UI) 708.

In an embodiment of the invention, the apparatus 700 is exercise equipment, such as a treadmill, an exercise bike and/or cross-training equipment.

In an embodiment of the invention, the apparatus 700 is a sport computer, such as a heart rate monitor, activity monitor, and/or a bike computer.

In an embodiment of the invention, the apparatus is a circuit board which may be provided for larger equipment, such as exercise equipment.

The processing unit 704 receives input data 702, such as exercise intensity information, user information, training load information, energy substrate information and other data described in conjunction with the methods. The processing unit 704 executes a computer process according to methods, wherein the method may be stored in the memory unit 707 as computer readable encoded instructions.

The user interface 708 may comprise input devices, such as a keyboard or keypad, for obtaining user commands and information according to the methods. The user interface 708 may further comprise an output device, such as a display, for displaying the user output parameters in accordance to the method. Such output parameters include training load, recovery time, and graphs, such as those shown FIGS. 5a to 5d.

In an embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments, the methods described herein may be implemented by software programs tangibly embodied in a processor-readable medium and may be executed by a processor. Further, in an exemplary, non-limited embodiment, implementations can include distributed processing, component/object distributed processing, and parallel processing. Alternatively, virtual computer system processing can be constructed to implement one or more of the methods or functionality as described herein.

It is also contemplated that a computer-readable medium includes instructions or receives and executes instructions responsive to a propagated signal, so that a device connected to a network can communicate voice, video or data over the network. Further, the instructions may be transmitted or received over the network via the network interface device.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk, tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

Although specific example embodiments have been described, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

What is claimed is:

1. A method of providing a user's recovery time on an electronic activity monitor in response to an exercise, the method comprising:
   determining, using a sensing device, exercise intensity associated with the user, the sensing device comprising at least one of a heart rate information sensing device, GPS positioning device, and movement sensor;
   determining, using the electronic activity monitor, protein combustion information $E_{PRO,i}$ during the exercise associated with the user at an instant i in accordance with the following equation $$E_{PRO,i} = E_{CHO,Ri} + E_{CHO,i} \qquad (3)$$

$E_{CHO,Ri}$ representing dynamic carbohydrate reserve information at instant i, $E_{CHO,i}$ representing carbohydrate consumption rate at instant i, the $E_{CHO,i}$ being determined using a combustion curve and the exercise intensity, the $E_{CHO,Ri}$ being obtained using the exercise intensity, the combustion curve representing protein combustion as a function of the exercise intensity, the combustion curve being selected based on carbohydrate reserve associated with the user during the exercise, the carbohydrate reserve representing an amount of carbohydrates available for energy combustion in the user's body, the exercise intensity being a measurable variable that is a function of at least one of a heart rate parameter, internal temperature, speed, and type of exercise;
   determining, using the electronic activity monitor, a training load value that indicates the user's training load based on the computed protein combustion information $E_{PRO,i}$, the training load being proportional to a sum of accumulated protein consumption and carbohydrate consumption during the exercise;
   determining, using the electronic activity monitor, a recovery time required by the user to recover from the exercise using the training load value; and
   displaying, using a display device, the recovery time.

2. A method of determining a user's training load defined by claim 1, wherein the dynamic carbohydrate reserve information is determined using a carbohydrate combustion model and an initial carbohydrate reserve information, the initial carbohydrate reserve information representing the user's carbohydrate reserve at a beginning of at least one exercise session.

3. A method of determining a user's training load defined by claim 1, wherein the protein combustion information is determined using nutritional intake information associated with the user, the nutritional intake information representing nutritional intake associated with the user during at least one exercise session.

4. A method of determining a user's training load defined by claim 1, wherein the protein combustion information is determined by using a total energy expenditure and a fat combustion model.

5. A method of determining a user's training load defined by claim 1, further comprising determining the user's training load based on a mechanical stimulus, the mechanical stimulus representing mechanical stress experienced by the user and being associated with at least one exercise session.

6. A method of determining a user's training load defined by claim 1, further comprising determining the user's training load based on a modality, the modality representing exercise type and being associated with at least one exercise session.

7. A method of determining a user's training load defined by claim 1, further comprising displaying the training load on a display device.

8. A method of determining a user's training load defined by claim 1, further comprising determining recovery time required by the user to recover from the exercise, wherein the recovery time is computed from the training load.

9. A method of determining a user's training load defined by claim 1, wherein the protein combustion information is determined from the exercise intensity information with respect to an aerobic threshold and an anaerobic threshold of the user.

10. A method of determining a user's training load defined by claim 1, wherein the exercise intensity information is determined from at least one of the following parameters associated with the user and measured during the exercise: heart rate, activity, running speed, and cycling speed.

11. An apparatus to that provides a user's recovery time on an electronic activity monitor in response to an exercise, the apparatus comprising:
    determining, using a sensing device, exercise intensity associated with the user, the sensing device comprising at least one of a heart rate information sensing device, GPS positioning device, and movement sensor;
    determining, using the electronic activity monitor, protein combustion information $E_{PRO,i}$ during the exercise associated with the user at an instant i in accordance with the following equation $$E_{PRO,i} = E_{CHO,Ri} + E_{CHO,i} \qquad (3)$$

$E_{CHO,Ri}$ representing dynamic carbohydrate reserve information at instant i, $E_{CHO,i}$ representing carbohydrate consumption rate at instant i, the $E_{CHO,i}$ being determined using a combustion curve and the exercise intensity, the $E_{CHO,Ri}$ being obtained using the exercise intensity, the combustion curve representing protein combustion as a function of the exercise intensity, the combustion curve being selected based on carbohydrate reserve associated with the user during the exercise, the carbohydrate reserve representing an amount of carbohydrates available for energy combustion in the user's body, the exercise intensity being a measurable variable that is a function of at least one of a heart rate parameter, internal temperature, speed, and type of exercise;

determining, using the electronic activity monitor, a training load value that indicates the user's training load based on the protein combustion information $E_{PRO,i}$, the training load being proportional to a sum of accumulated protein consumption and carbohydrate consumption during an exercise session;

determining, using the electronic activity monitor, a recovery time required by the user to recover from the exercise using the training load value; and displaying, using a display device, the recovery time.

12. An apparatus to determine a user's training load defined by claim 11, wherein the carbohydrate reserve determination unit determines the dynamic carbohydrate reserve information using a carbohydrate combustion model and an initial carbohydrate reserve information, the initial carbohydrate reserve information representing the user's carbohydrate reserve at a beginning of at least one exercise session.

13. An apparatus to determine a user's training load defined by claim 11, wherein the protein combustion determination unit computes the protein combustion information from the exercise intensity information with respect to an aerobic threshold and an anaerobic threshold of the user.

14. An apparatus to determine a user's training load defined by claim 11, wherein the measured exercise intensity information comprises at least one of the following parameters associated with the user and measured during the exercise: heart rate, activity, running speed, and cycling speed.

15. A non-transitory computer-readable storage medium comprising encoded instructions that, when executed by a computing device, cause the computing device to a user's recovery time on an electronic activity monitor by performing operations comprising:

determining, using a sensing device, exercise intensity associated with the user, the sensing device comprising at least one of a heart rate information sensing device, GPS positioning device, and movement sensor;

determining, using the electronic activity monitor, protein combustion information $E_{PRO,i}$ during the exercise associated with the user at an instant i in accordance with the following equation $$E_{PRO,i}=E_{CHO,Ri}+E_{CHO,i} \quad (3)$$

$E_{CHO,Ri}$ representing dynamic carbohydrate reserve information at instant i, $E_{CHO,i}$ representing carbohydrate consumption rate at instant i, the $E_{CHO,i}$ being determined using a combustion curve and the exercise intensity, the $E_{CHO,Ri}$ being obtained using the exercise intensity, the combustion curve representing protein combustion as a function of the exercise intensity, the combustion curve being selected based on carbohydrate reserve associated with the user during the exercise, the carbohydrate reserve representing an amount of carbohydrates available for energy combustion in the user's body, the exercise intensity being a measurable variable that is a function of at least one of a heart rate parameter, internal temperature, speed, and type of exercise;

determining, using the electronic activity monitor, a training load value that indicates the user's training load based on the computed protein combustion information $E_{PRO,i}$, the training load being proportional to a sum of accumulated protein consumption and carbohydrate consumption during the exercise;

determining, using the electronic activity monitor, a recovery time required by the user to recover from the exercise using the training load value; and displaying, using a display device, the recovery time.

16. A non-transitory computer-readable storage medium defined by claim 15, wherein the operations further comprise determining the dynamic carbohydrate reserve information using a carbohydrate combustion model and an initial carbohydrate reserve information, the initial carbohydrate reserve information representing the user's carbohydrate reserve at a beginning of at least one exercise session.

17. A non-transitory computer-readable storage medium defined by claim 15, wherein the operations further comprise determining protein combustion information using nutritional intake information associated with the user, the nutritional intake information representing nutritional intake associated with the user during at least one exercise session.

18. A non-transitory computer-readable storage medium defined by claim 15, wherein the operations further comprise determining the protein combustion information by using a total energy expenditure and a fat combustion model.

19. A non-transitory computer-readable storage medium defined by claim 15, wherein the operations further comprise determining the user's training load based on a mechanical stimulus, the mechanical stimulus representing mechanical stress experienced by the user and being associated with at least one exercise session.

20. A non-transitory computer-readable storage medium defined by claim 15, wherein the operations further comprise determining the user's training load based on a modality, the modality representing exercise type and being associated with at least one exercise session.

21. A non-transitory computer-readable storage medium defined by claim 15, wherein the operations further comprise displaying the training load on a display device.

22. A non-transitory computer-readable storage medium defined by claim 15, wherein the operations further comprise determining recovery time required by the user to recover from the exercise, wherein the recovery time is computed from the training load.

23. A non-transitory computer-readable storage medium defined by claim 15, wherein the operations further comprise determining the protein combustion information from the exercise intensity information with respect to an aerobic threshold and an anaerobic threshold of the user.

24. A non-transitory computer-readable storage medium defined by claim 15, wherein the operations further comprise determining the exercise intensity information from at least one of the following parameters associated with the user and measured during the exercise: heart rate, activity, running speed, and cycling speed.

* * * * *